United States Patent
Sun et al.

(10) Patent No.: US 9,687,657 B2
(45) Date of Patent: Jun. 27, 2017

(54) PACEMAKER SIGNAL DETECTING METHOD, PACEMAKER SIGNAL DETECTING SYSTEM AND ELECTROCARDIAL DETECTING DEVICE

(71) Applicant: Shenzhen Mindray Bio-Medical Electronics Co., Ltd., Shenzhen (CN)

(72) Inventors: Ze-Hui Sun, Shenzhen (CN);
Xiao-Wen Cheng, Shenzhen (CN);
Ming-Shi Ding, Shenzhen (CN);
Qi-Ling Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

(21) Appl. No.: 14/737,421

(22) Filed: Jun. 11, 2015

(65) Prior Publication Data

US 2015/0283387 A1    Oct. 8, 2015

Related U.S. Application Data

(63) Continuation of application No. PCT/CN2013/083098, filed on Sep. 9, 2013.

(30) Foreign Application Priority Data

Dec. 11, 2012    (CN) .......................... 2012 1 0531994

(51) Int. Cl.
*A61N 1/37* (2006.01)
*A61N 1/365* (2006.01)
*A61B 5/0452* (2006.01)

(52) U.S. Cl.
CPC .......... *A61N 1/3702* (2013.01); *A61B 5/0452* (2013.01); *A61N 1/36507* (2013.01); *A61N 1/3704* (2013.01)

(58) Field of Classification Search
CPC ........ A61N 1/3706; A61N 1/37; A61N 1/362; A61N 1/36132; A61N 1/36135; A61N 1/025; A61N 1/36178; A61N 1/37252; A61N 1/08; A61N 1/36; A61N 1/365; A61B 5/0452; A61B 5/7264;
(Continued)

(56) References Cited

U.S. PATENT DOCUMENTS 5,682,902 A    11/1997  Herleikson
6,304,772 B1   10/2001  Taha et al.
7,336,998 B2    2/2008  Yonce

FOREIGN PATENT DOCUMENTS

CN    102028459 A     4/2011
WO    2005101229 A1  10/2005

*Primary Examiner* — Deborah Malamud
(74) *Attorney, Agent, or Firm* — Steven Reiss

(57) ABSTRACT

The present invention provides a pacemaker signal detecting method, a pacemaker signal detecting system, and an electrocardial detecting device. The pacemaker signal detecting system pre-processes an original pacemaker signal separated from a pacemaker electrocardial signal, calculates a number of basic morphological features based on the pre-processed original pacemaker signal, confirms an authenticity of a pacemaker signal according to the calculated basic morphological features, and records positions of the true pacemaker signal has been confirmed. The basic morphological features include a width, a slew rate, and amplitude of the pacemaker signal. The electrocardial detecting device of the present invention can detect the pacemaker signal more precisely and output the electrocardial signal marked with the pacemaker signal.

19 Claims, 15 Drawing Sheets

(58) Field of Classification Search
CPC ... A61B 5/0402; A61B 5/7221; A61B 5/7282; A61B 5/0006; A61B 5/00; A61B 5/04012; A61B 5/04017; A61B 5/04028; A61B 5/7203; A61B 5/7235; A61B 5/04; A61B 5/4836; A61B 5/486; G06F 19/3418; G06F 19/3406; G06K 9/0053; G06K 9/0055; G06Q 50/22; Y10S 128/92; Y10S 128/923
See application file for complete search history.

PACEMAKER SIGNAL DETECTING METHOD, PACEMAKER SIGNAL DETECTING SYSTEM AND ELECTROCARDIAL DETECTING DEVICE

CROSS-REFERENCE TO RELATED APPLICATIONS

This application claims all benefits accruing under 35 U.S.C. §119 from China Patent Application No. 201210531994.0, filed on Dec. 11, 2012 in the China Intellectual Property Office, the content of which is hereby incorporated by reference. This application is a continuation under 35 U.S.C. §120 of international patent application No. PCT/CN2013/083098, filed on Sep. 9, 2013.

BACKGROUND

1. Field

The present invention relates to medical technologies, and particularly, to a pacemaker signal detecting method, a pacemaker signal detecting system, and an electrocardial detecting device.

2. Background

Bradycardia means low cardiac frequency, probably accompanied by rhythm disturbance. The cardiac frequency of the bradycardia is normally lower than sixty beats per minute. A heart of a patient suffering from serious bradycardia cannot provide enough oxygen-rich blood to the body. As a result, the patient shows symptoms of dizziness, hyposthenia, shortness of breath, and even syncope, which adversely affects living quality of the patient and may endanger the life of the patient. Pacemaker implantation is a common therapeutic solution to the bradycardia. A pacemaker transmits a small electric signal to the heart to increase the cardiac frequency, helping the heart to recover to a normal rhythm and relieve the symptoms of bradycardia. Electrocardial detecting devices or electrocardial diagnostic devices, such as an electrocardiograph, provide a non-invasive and quick way to detect a pacemaker signal, and they may also be used in patient monitoring and other aspects, such as patient recognizing and diagnosing after the pacemaker is implanted.

A detecting range of the pacemaker signal is specified in an electrocardial monitoring standard and an electrocardiograph standard, wherein the detecting range of the pacemaker signal to a patient monitor is 0.1 millisecond (ms) to 0.2 ms in width and ±2 millivolt (my) to ±700 my in amplitude. However, because the pacemaker is an implanted device, power supply is a main problem needed to be solved by the pacemaker. In order to increase service life of a battery of the pacemaker, pacemaker manufacturers need to reduce the power consumption of the pacemaker and improve efficiency of the pacemaker. Such improvements may increase the service life of the battery, but effectively lead to smaller amplitudes of the pacemaker signal when measured at the body surface and difficulty in detecting the pacemaker signal.

Furthermore, due to projection relationships between the pacemaker signal and different electrocardial lead axis, the amplitude of the pacemaker signal in the different electrocardial lead axis show great differences thereamong when the pacemaker signal is conducted to, and measured at, the body surface. With development of the pacemaker technology, a pacemaker which meets related standards cannot completely meet demands of clinical use. American Electrocardiology Society also advises that monitoring device manufacturers should improve detection of the pacemaker signal. Currently, most of the monitoring device manufacturers apply a hardware method to detect the pacemaker signal. A basic principle of the hardware method is to detect slew rate and amplitude of the pacemaker signal. However, since a strategy of detection by hardware is very simplistic, the shapes of the pacemaker signals cannot be detected and the hardware method also fails to adaptively adjust detection threshold based on changes of the pacemaker signal and ambient noise. Thus, the hardware method is very vulnerable to interference. Some manufacturers compromise the threshold detection values to improve the immunity of the interference on a pacemaker signal detecting module, but that lowers the sensitivity of detection.

SUMMARY

The main technical problem to be solved by the present invention is to provide a pacemaker signal detecting method, a pacemaker signal detecting system, and an electrocardial detecting device using the method and system to detect a pacemaker signal more precisely.

A first aspect of this application is a pacemaker signal detecting method. The pacemaker signal detecting method includes following steps:

acquiring a pacemaker electrocardial signal;

separating a pacemaker signal from the pacemaker electrocardial signal in a selected detecting channel to get an original pacemaker signal; and detecting a true pacemaker signal based on the original pacemaker signal, the detection requiring:

pre-processing the original pacemaker signal;

calculating a plurality of basic morphological features of the pacemaker signal based on the pre-processing of the original pacemaker signal, wherein the basic morphological features comprise a width, a slew rate, and an amplitude of the pacemaker signal;

confirming an authenticity of the pacemaker signal based on the basic morphological features of the pacemaker signal; and recording positions of the pacemaker signal has been confirmed as the true pacemaker signal.

A second aspect of this application is a pacemaker signal detecting system. The pacemaker signal detecting method includes following modules:

a pre-processing module configured to pre-process an original pacemaker signal separated from a pacemaker electrocardial signal;

a pacemaker signal detecting module configured to calculate a plurality of basic morphological features of the pacemaker signal based on the pre-processed original pacemaker signal and confirm the authenticity of the pacemaker signal based on the basic morphological features. The basic morphological features which comprise a width, a slew rate, and an amplitude of the pacemaker signal; and a marking module configured to mark the pacemaker signal and record positions mark of the pacemaker signal after the same has been confirmed as the true pacemaker signal.

A third aspect of the present invention is an electrocardial detecting device. The electrocardial detecting device includes:

a signal acquiring system configured to acquire a pacemaker electrocardial signal and separate an original pacemaker signal and an electrocardial signal from the pacemaker electrocardial signal;

an electrocardial signal pre-processing system configured to pre-process the electrocardial signal;

the pacemaker signal detecting system mentioned above;

an electrocardial analysis system configured to mark positions of a pacemaker signal detected by the pacemaker signal detecting system; and an output system configured to output the electrocardial signal marked with the pacemaker signal.

BRIEF DESCRIPTION OF THE DRAWINGS

The present invention is illustrated by way of embodiments and accompanying drawings.

DETAILED DESCRIPTION

In general, the word "module", as used herein, refers to logic embodied in hardware or firmware, or to a collection of software instructions, written in a programming language, such as, Java, C, or assembly. One or more software instructions in the modules may be embedded in firmware, such as in an EPROM. The modules described herein may be implemented as either software and/or hardware modules and may be stored in any type of non-transitory computer-readable medium or other storage device. Some non-limiting examples of non-transitory computer-readable median include CDs, DVDs, BLU-RAY, flash memory, and hard disk drives.

A pacemaker signal means a signal generated by a pacemaker.

A pacemaker electrocardial signal means an electrocardial signal including the pacemaker signals.

An original pacemaker signal means a pacemaker signal sequence separated from the pacemaker electrocardial signal and without confirmation of authenticity.

A pacemaker signal generated by a pacemaker is usually detected in a patient with an implanted pacemaker signal during electrocardial signal detection. The electrocardial signal including the pacemaker signal is called referred to as "the pacemaker electrocardial signal" in this disclosure. Whether it is an analysis of the electrocardial signal which is required or doing surveillance of the working of a pacemaker, the pacemaker signal needs to be separated from the pacemaker electrocardial signal of the electrocardial monitoring device or the electrocardial detecting device, such as an electrocardiograph.

Figure 1:
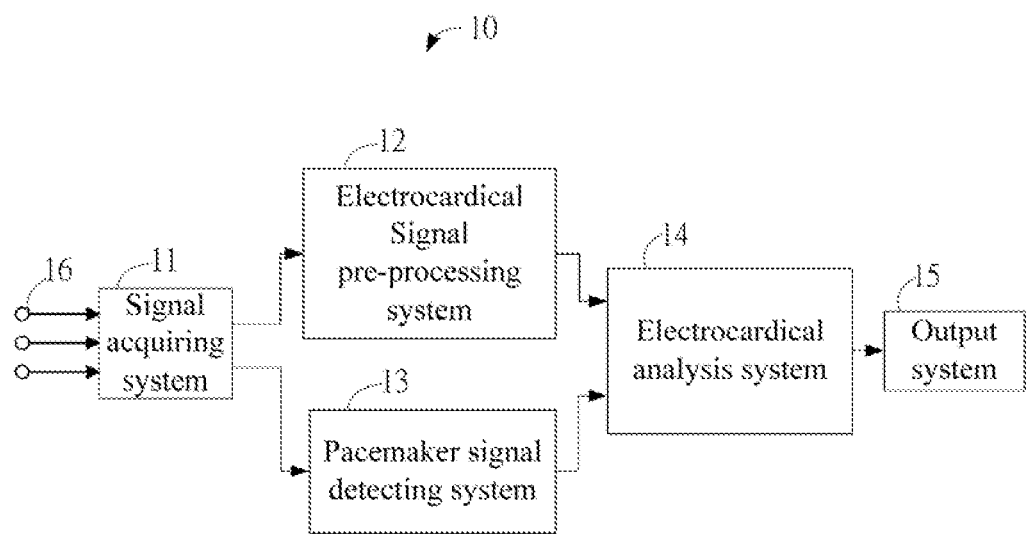
FIG. 1 is a block diagram view of an exemplary embodiment of an electrocardial detecting device.

Referring to FIG. 1, FIG. 1 illustrates a module block diagram of an electrocardial detecting device 10, which can be considered as a part of an electrocardial diagnostic device or a patient monitoring device. It can also be considered as an independent electrocardial detecting device 10. The electrocardial detecting device 10 includes a signal acquiring system 11, an electrocardial signal pre-processing system 12, an electrocardial analysis system 14, an output system 15, and a pacemaker signal detecting system 13. The electrocardial detecting device 10 detects the pacemaker signal and marks a result of detecting the pacemaker signal in an analysis result of the electrocardial signal.

The pacemaker electrocardial signal is picked up by a number of electrodes 16 and transmitted to the signal acquiring system 11. The signal acquiring system 11 separates the original pacemaker signal and the electrocardial signal from the pacemaker electrocardial signal and outputs the original pacemaker signal to the pacemaker signal detecting system 13. The electrocardial signal is also output to the electrocardial signal pre-processing system 12.

The electrocardial signal pre-processing system 12 pre-processes the electrocardial signal in an electrocardial signal sequence and outputs the pre-processed electrocardial signal to the electrocardial analysis system 14. The electrocardial analysis system 14 analyzes the electrocardial signal.

The pacemaker signal detecting system 13 processes the original pacemaker signal, confirms the authenticity of the pacemaker signal, and records the positions of true pacemaker signals. The pacemaker signal detecting system 13 also generates a pacemaker signal mark, and transmits the pacemaker signal mark to the electrocardial analysis system 14. The electrocardial analysis system 14 marks the result of the pacemaker signal detecting system 13 in the electrocardial signal.

The output system 15 outputs the electrocardial signal marked with the pacemaker signal.

Figure 2:
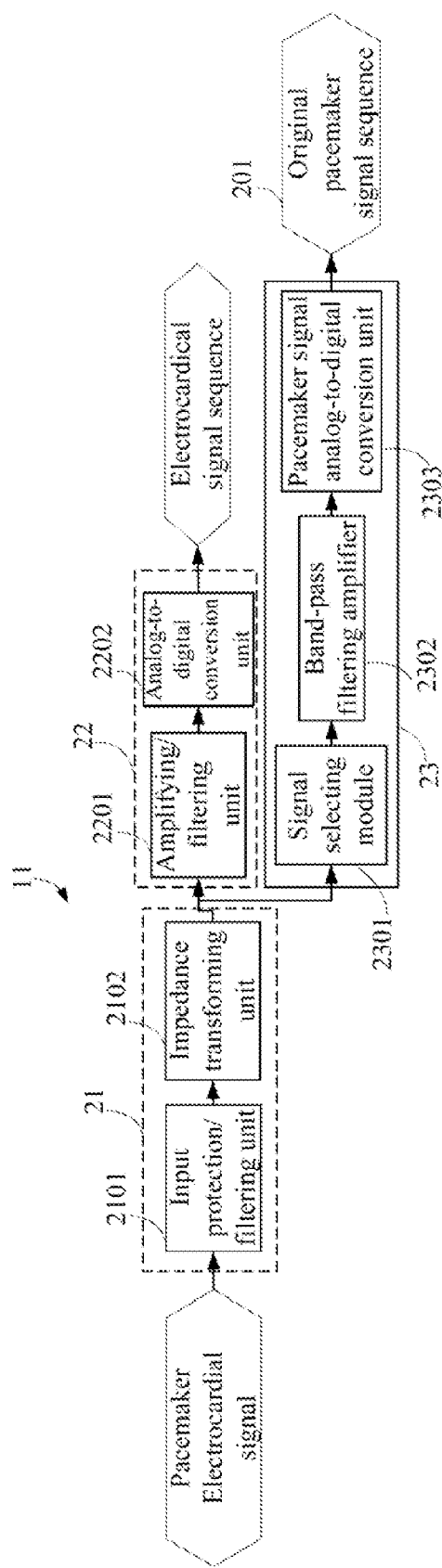
FIG. 2 is a block diagram view of a signal acquiring system of the electrocardial detecting device of FIG. 1.

A detailed structure of the signal acquiring system 11 is illustrated in FIG. 2. The signal acquiring system 11 is composed of an electrocardial input module 21, an electrocardial collecting module 22, and a pacemaker signal collecting module 23. The electrocardial input module 21 includes an input protection/filtering unit 2101 and an impedance transforming unit 2102. The electrocardial signal collecting module 22 includes an amplifying/filtering unit 2201 and an analog-to-digital conversion unit 2202. The pacemaker signal collecting module 23 includes a signal selecting unit 2301, a band-pass filtering amplifier 2302, and a pacemaker signal analog-to-digital conversion unit 2303. The band-pass filtering amplifier 2302 selects the signal according to a difference between a frequency component of the pacemaker signal and a frequency component of the electrocardial signal. The pacemaker signal analog-to-digital conversion unit 2303 outputs the original pacemaker signal sequence 201. Finally, the signal acquiring system 11 outputs two data sequences, that is, the electrocardial signal sequence and the original pacemaker signal sequence 201.

In order to more precisely recognize the pacemaker signal, the pacemaker signal detecting system 13 executes further process to the original pacemaker signal separated from the pacemaker electrocardial signal. After the pre-processing of the original pacemaker signal, the pacemaker signal detecting system 13 calculates a number of basic morphological features of the pacemaker signal based on the pre-processed original pacemaker signal and confirms the authenticity of the pacemaker signal according to the basic morphological features of the pacemaker signal. Thus, the probabilities of error and misjudgment in relation to the pacemaker signal are reduced and the pacemaker signal can be detected more precisely. A pacemaker signal detecting method used by the pacemaker signal detecting system 13 is illustrated below.

First Embodiment

Figure 3:
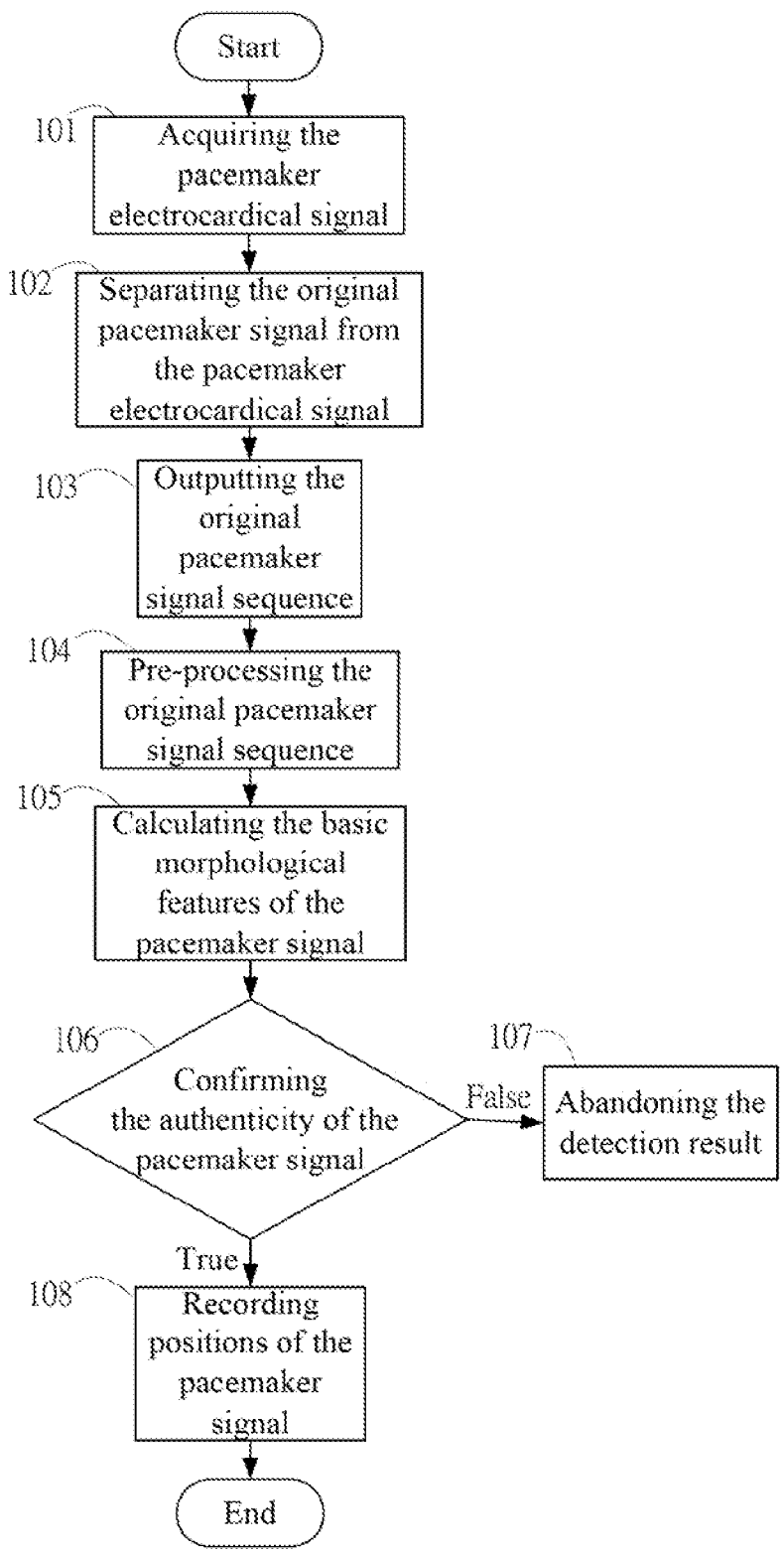
FIG. 3 is a flowchart of a first embodiment of a pacemaker signal detecting method.

Referring to FIG. 3, the pacemaker signal detecting method of this embodiment includes following steps:

Step 101, acquiring the pacemaker electrocardial signal. In detail, the pacemaker electrocardial signal is picked up by the electrodes 16. The pacemaker electrocardial signal is extracted by being passed through a protection circuit, a filtering circuit, and an impedance transforming circuit.

Step 102, separating the original pacemaker signal from the pacemaker electrocardial signal extracted in step 101. In detail, the pacemaker electrocardial signal is passed through a high-pass hardware filter or a band-pass hardware filter. The electrocardial signal is filtered out thus leaving the pure original pacemaker signal.

Step 103, outputting the original pacemaker signal sequence 201. In detail, the remaining original pacemaker signal is converted from analog data to digital data to get the original pacemaker signal sequence 201.

Step 104, the original pacemaker signal sequence 201 is pre-processed to highlight the features of the pacemaker signal.

Step 105, the basic morphological features of the pacemaker signal are calculated according to the pre-processed original pacemaker signal. The basic morphological features include a width, a slew rate, and an amplitude of the pacemaker signal.

Step 106, the authenticity of the pacemaker signal is confirmed based on the basic morphological features of the pacemaker signal.

Step 107, when step 106 reveals the pacemaker signal to be a false pacemaker signal, that is, that the pacemaker signal is invalid, the result of detection is abandoned in this case.

Step 108, when the pacemaker signal is confirmed as a true pacemaker signal by step 106, that is, that the pacemaker signal is valid, positions of the true pacemaker signal are recorded.

Figure 4:
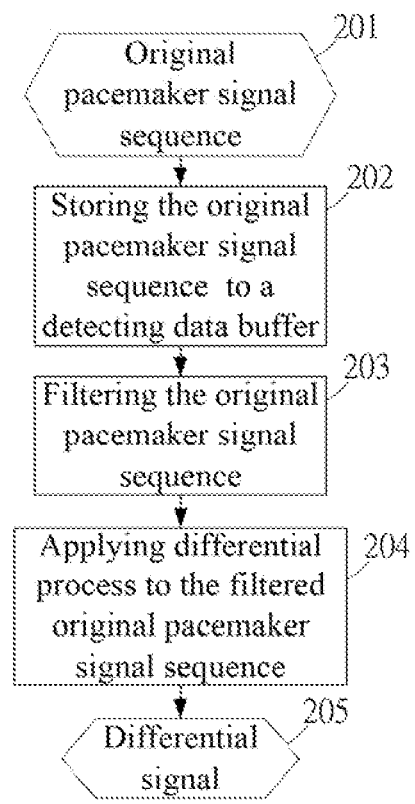
FIG. 4 is a flowchart of an exemplary embodiment of a pre-processing step in the pacemaker signal detecting method.

The sub-steps of step 104, referring to FIG. 4, in an embodiment of the pre-process for the original pacemaker signal sequence 201, includes following steps:

Step 202, storing the original pacemaker signal sequence 201 with a fixed length to a detecting data buffer, which can avoid taking up too much processor resource in a high sampling frequency. For example, the original pacemaker signal can be set to be detected once every 2 milliseconds (ms). That is, the original pacemaker signal with a 2 ms length is stored in the data buffer when the original pacemaker signal is detected. If the original pacemaker signal is set to be detected once every 4 ms, the fixed length of the original pacemaker signal sequence 201 will be set as 4 ms.

Step 203 should preferably be executed after step 202. The filtering of the original pacemaker signal sequence 201 can be by a high-pass filter or by a band-pass filter. A band-pass filter can include a low-pass filter and a high-pass filter.

The original pacemaker signal is subtracted by a signal being filtered by an average filter process when the high-pass filter is employed. The number of signals for the average filter process can be changed according to specific requirement. The filtering process is illustrated below by taking the average filtering of sixteen signals as an example.

The original pacemaker signal is defined as x(n). The high-pass filtered original pacemaker signal is defined as x_hpf(n), thus x_hpf(n) can be calculated by a formula (1):

$$x\_hpf(n)=x(n)-[x(n)+x(n-1)+ \ldots +x(n-15)]/16 \quad (1)$$

The high-pass filter can effectively suppress low frequency noise, such as power frequency interference, QRS complex wave, low and medium frequency myoelectricity, and so on. A portion of residual interference will remain after a hardware high-pass filtering process when the pacemaker signal includes larger interference signals. The detection of the pacemaker signal is adversely affected. Therefore, the original pacemaker signal is filtered again by software in step 203 in order to reduce the adverse effect on detection made by power frequency interference, myoelectricity, QRS complex wave, and so on. At the same time, the software filter is more flexible than the hardware filter and can be conveniently adjusted according to different applications.

Step 204, applying a differential process to the filtered original pacemaker signal sequence 201 to get a differential signal 205. It is understood that, in step 204, differential process can be directly applied to the original pacemaker signal when the filtering process in step 203 is omitted. The differential process can be executed in two signals, four signals, or sixteen signals. In this embodiment, differential process by two signals is taken as example. In detail, the differential signal 205 is defined as y(n) which can be calculated by a formula (2):

$$y(n)=x\_hpf(n)-x\_hpf(n-2) \quad (2)$$

The differential process extracts slew rate of the original pacemaker signal by a differential operation. The differential operation can remove noise of low slew rate and effectively highlight features of the pacemaker signal.

Figure 5:
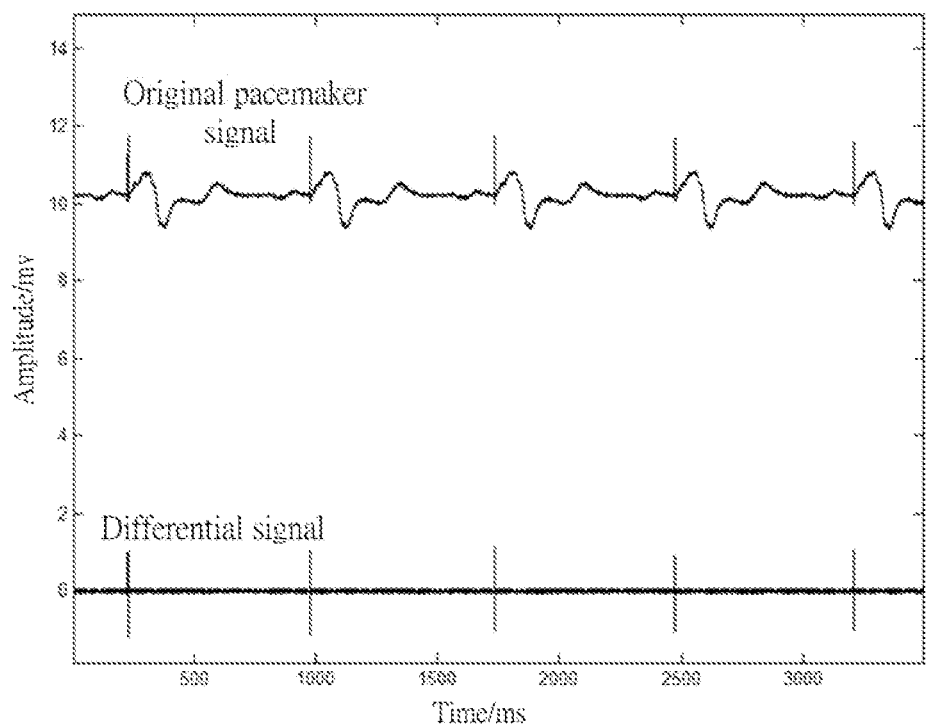
FIG. 5 is an oscilloscope view of an exemplary embodiment of an original pacemaker signal and a differential signal of the original pacemaker signal.

Referring to FIG. 5, the original pacemaker signal (in an upper diagram) is compared with the high-pass differential signal 205 (in a lower diagram). The features of pacemaker signal are effectively highlighted after the original pacemaker signal has been high-pass filtered and subjected to differential process.

Figure 6:
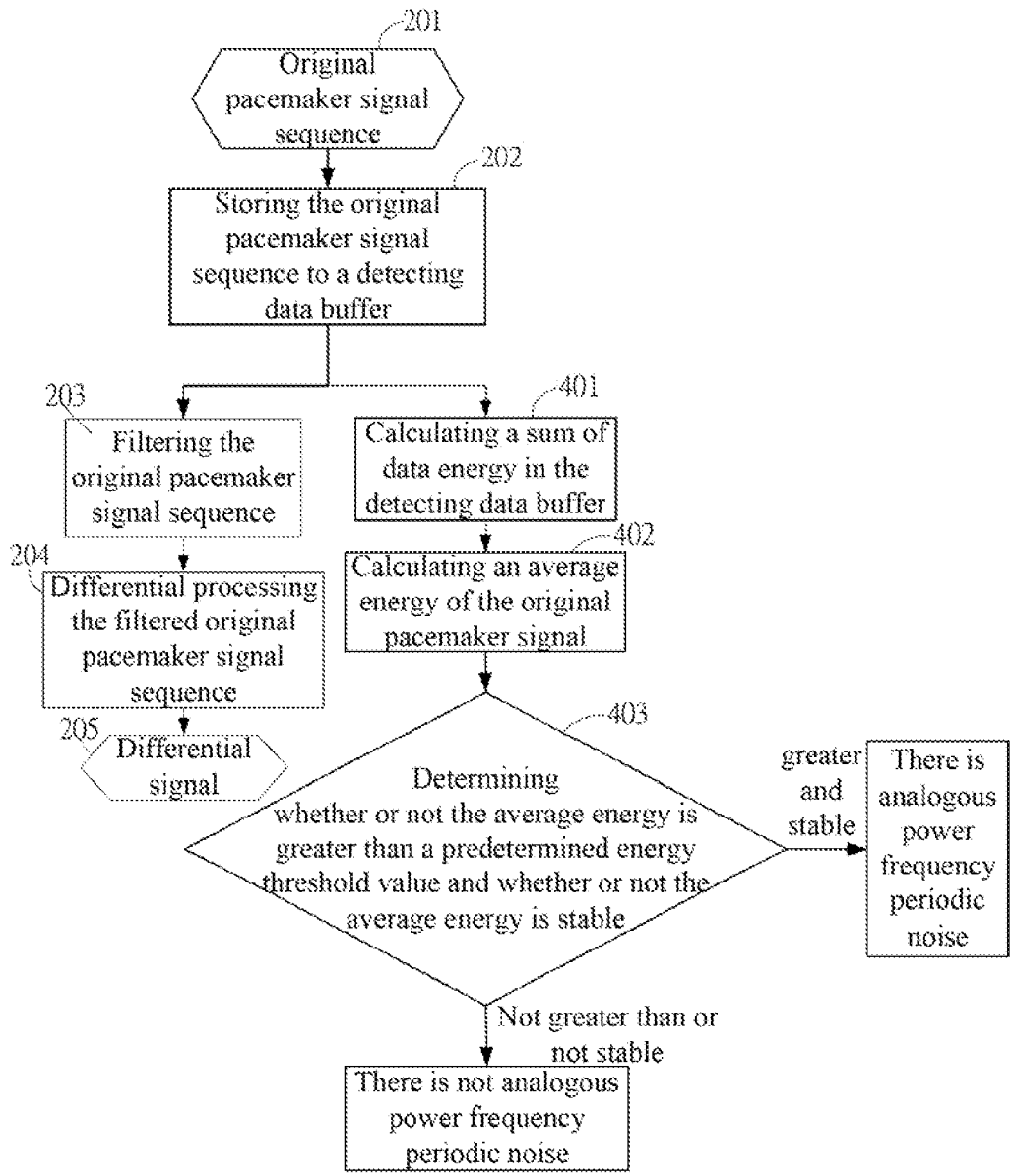
FIG. 6 is a flowchart of other embodiment of a pre-processing step in the pacemaker signal detecting method.

Referring to FIG. 6, in other embodiment, in the pre-processing step, the original pacemaker signal sequence 201 can also be checked to determine whether or not there is noise in the original pacemaker signal sequence 201. This can suggest different calculating strategies according to the noise. For example, step 104 for pre-processing the original pacemaker signal sequence 201 can further include following steps:

Step 401, calculating a sum of data energy in the detecting data buffer where the sum of data energy means a sum of absolute values of signals of the original pacemaker signal sequence 201 stored in the detecting data buffer.

Step 402, calculating an average energy of the original pacemaker signal sequence 201 in the detecting data buffer according to the sum of data energy calculated in step 401.

Step 403, determining whether or not the average energy calculated in step 402 is greater than a predetermined energy threshold value and establishing whether or not the average energy is stable according to an average energy fluctuation in a predetermined time period. It is determined that there is the analogous power frequency periodic noise in the original pacemaker signal sequence 201 if the average energy value is greater than the energy threshold value and remains stable. Otherwise, it is determined that there is no the analogous power frequency periodic noise in the original pacemaker signal sequence 201. The energy threshold value is predetermined according to specific need. In one embodiment, the energy threshold value is set as a maximum value of the average energy when there is no the analogous power frequency periodic noise.

The basic morphological features of the pacemaker signal are calculated based on the differential signal 205 and the original pacemaker signal sequence 201. The basic morphological features of the pacemaker signal. In one embodiment, the basic morphological features are calculated according to a start, a terminal, and a peak of the pacemaker signal. The peak of the pacemaker signal means a point of the pacemaker signal with a maximum amplitude in an absolute value along a direction of the pacemaker signal. The start of the pacemaker signal means an amplitude stable point, a reversal point, or an inflection point of the pacemaker signal, detected by checking backwards from the peak of the pacemaker signal in a reverse chronological order of detections. The terminal of the pacemaker signal means an amplitude stable point, a reversal point, or an inflection point of the pacemaker signal detected by checking forwards from the peak of the pacemaker signal in the chronological order of detections.

In one embodiment, the detection of the pacemaker signal is executed by using the original pacemaker signal and the high-pass differential signal 205 acquired in the pre-processing of the original pacemaker signal. At first, this is done to detect a number of key points of the pacemaker signal on the original pacemaker signal and the high-pass differential signal 205. Secondly, the basic morphological features of the pacemaker signal are calculated using the detected key points. And then, to determine whether the signal is a true pacemaker signal or part of a true pacemaker signal, or is simply noise, by confirming the basic morphological features of the pacemaker signal. Finally, to output a marking of the single channel pacemaker signal according to the result of confirming. In this embodiment, the basic morphological features of the pacemaker signal are calculated by detecting the key points, such as a first boundary point A, a zero crossing point B, a first maximum value point C, a start D, a second boundary point X, a terminal E, a peak G, and so on.

Figure 7:
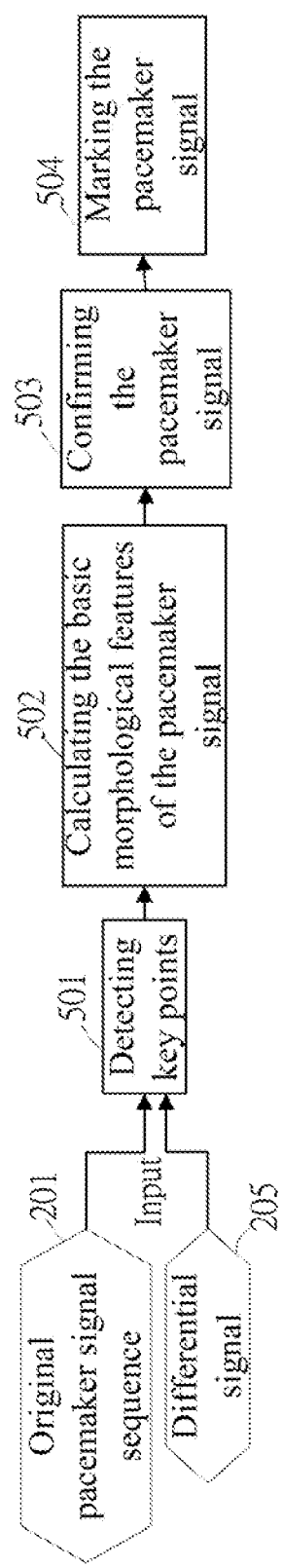
FIG. 7 is a flowchart of an exemplary embodiment of sub-steps of the calculating basic morphological features step in the pacemaker signal detecting method.

Referring to FIG. 7, step 105 and step 106 of FIG. 3, that is, the calculating of the basic morphological features and the determination of the authenticity of the pacemaker signal includes following steps:

Step 501, at first, the start and the terminal of the pacemaker signal is detected based on the differential signal 205. The start and the terminal of the pacemaker signal in the differential signal 205 are respectively corresponding to the start and the terminal of the pacemaker signal in the original pacemaker signal sequence 201. And then, to search the peak of the pacemaker signal between the start and the terminal of the original pacemaker signal sequence 201.

Figure 8:
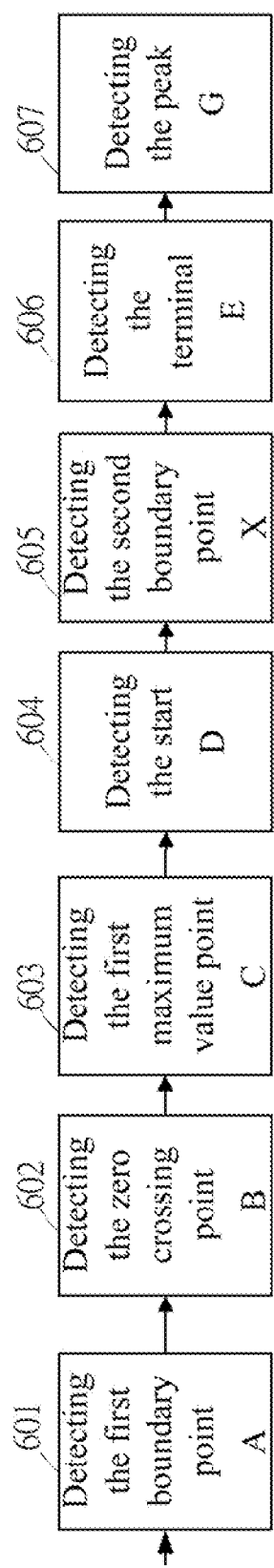
FIG. 8 is a flowchart of an exemplary embodiment of sub-steps of the key point detecting step in the pacemaker signal detecting method.

Referring to FIG. 8, to detect the start and the terminal of the pacemaker signal based on the differential signal 205 includes following steps:

Step 601, detecting the first boundary point A on the differential signal 205 in the chronological order of detection, the first boundary point A is a point on the differential signal 205 with an absolute value first time greater than the detection threshold value. At the same time, the direction of the pacemaker signal is determined according to the first boundary point A.

Step 602, searching the zero crossing point B after the first boundary point A in the chronological order of detection, the zero crossing point B is a first point of which the differential value sign is opposite to a differential value sign of a former point on the differential signal 205 after the first boundary point A. Preferably, a fix time period is set, to search the first point of which the differential value sign is opposite to a differential value sign of a former point on the different signal in the fix period after the first boundary point A. The zero crossing point B is defined when the first point of which the differential value sign is opposite to a differential value sign of a former point on the differential signal 205 after the first boundary point A is detected. The zero crossing point is defined as the last point on the differential signal 205 in the fix time period when the first point of which the differential value sign is opposite to a differential value sign of a former point on the differential signal 205 after the first boundary point A cannot be detected.

Step 603, searching a maximum value point with the same direction of the pacemaker signal between the first boundary point A and the zero crossing point B and defining the maximum value point as the first maximum value point C.

Step 604, searching the point satisfying conditions of the start D of the pacemaker signal and considering a point on the original pacemaker signal corresponding to the point satisfying conditions of the start of the pacemaker signal as the start D of the pacemaker signal. For example, the conditions of the start D can be differences between a differential value of a current point and differential values of three later points are greater than differences between the differential value of the current point and differential values of three former points; or a difference between the differential value of the current point and a differential value of a later point is greater than four times of a difference between the differential value of the current point and a differential value of a former point. The current point is considered as the start D if the current point satisfies these conditions of the start D. Of course, persons of ordinary skill are understood that, the conditions of the start D can be designed according to the specific requirement. The conditions of the start D may be different when the detecting method of the key points changes.

Step 605, detecting the differential signal 205 after the zero crossing point B to find the second boundary point X which satisfies conditions of the second boundary point X. For example, the conditions of the second boundary point X can be an absolute value of the differential value of the current point is greater than half of an absolute value of the differential value of the first maximum value point C and the direction of the current point is the same as the direction of the pacemaker signal. The current point is considered as the second boundary point X if satisfies these conditions. Of course, persons of ordinary skill are understood that, the conditions of the second boundary point X can be designed according to the specific requirement. The conditions of the second boundary point X may be different when the detecting method of the key points changes. Preferably, a fix time period is set, to detect a point satisfying the conditions of the second boundary point X in the fix time period after the zero crossing point B. The second boundary point X is defined when the point satisfying the conditions of the second boundary point X is detected. The first boundary point A is considered as interference if the point satisfying the conditions of the second boundary point X cannot be detected. Thus, this time detection of key point is terminated and then turn to step 601 to restart the detection of the first boundary point A with the absolute value greater than the detection threshold value.

Step 606, detecting a point satisfying conditions of the terminal E of the pacemaker signal after the second boundary point X and considering a point in the original pacemaker signal sequence 201 corresponding to the point satisfying conditions of the terminal E as the terminal E of the pacemaker signal. The conditions of the terminal E can be an amplitude value of a current point is close to or equal to an amplitude value of the start D. The current point satisfying these conditions is considered as the terminal E. Of course, persons of ordinary skill are understood that, the conditions of the terminal E can be designed according to the specific requirement. The conditions of the terminal E may be different when the detecting method of the key points changes. Preferably, a fix time period is set, to detect a point satisfying the conditions of the terminal E in the fix time period after the second boundary point X. The terminal E is defined when the point satisfying the conditions of the terminal E is detected. The terminal E is defined as the last point in the fix time period when the point satisfying the conditions of terminal E cannot be detected.

Step 607, searching the peak G between the start D and the terminal E of the original pacemaker signal sequence 201. Ordinary, a maximum value point having a direction the same as the direction of the pacemaker signal and between the start D and the terminal E of the original pacemaker signal is considered as the peak G of the pacemaker signal. The detection of the peak G can employ different method according to a judgment of whether or not there is the analogous power frequency periodic noise is detected in the pre-process. For example, when the judgment of there is the analogous power frequency periodic noise is made in the step 403, a point in the original pacemaker signal corresponding to the first maximum value point C detected in step 603 is considered as the peak G with a consideration of a large deformation of the pacemaker signal. When the judgment of there is not the analogous power frequency periodic noise is made in step 403, the maximum value point having a direction the same as the direction of the pacemaker signal and between the start D and the terminal E of the original pacemaker signal is considered as the peak G of the pacemaker signal.

Figure 9:
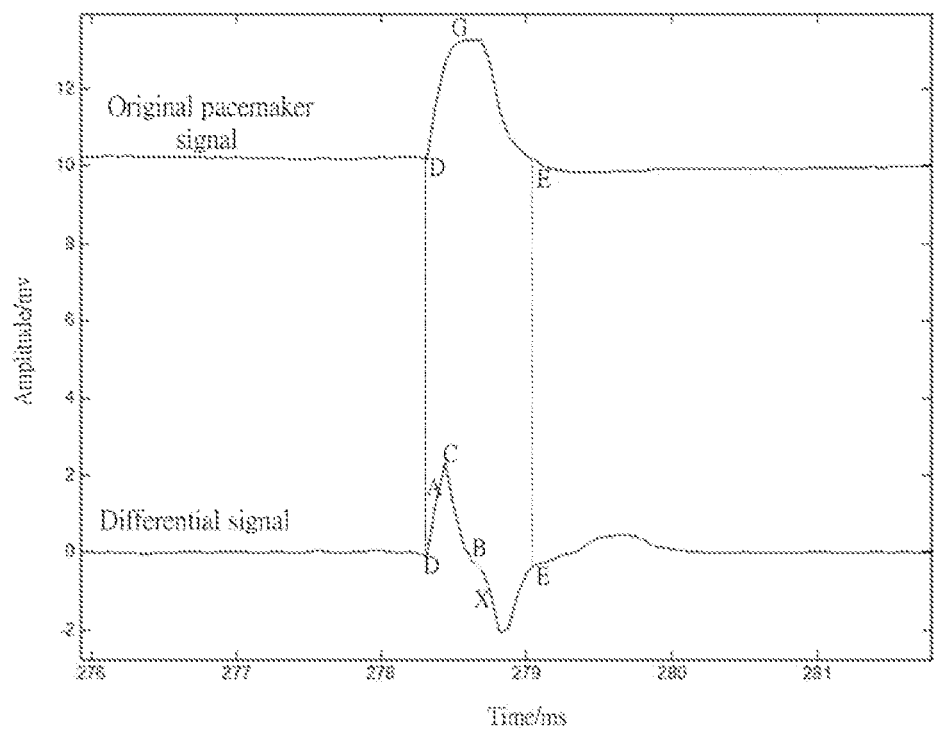
FIG. 9 is an oscilloscope view of an exemplary embodiment showing positions of a number of key points on the original pacemaker signal and the differential signal of the original pacemaker signal.

Positions of the key points detected in the original pacemaker signal and the differential signal 205 are illustrated in FIG. 9.

Step 502 is executed after the start D, the peak G, and the terminal E of the pacemaker signal is detected.

Step 502, calculating the basic morphological features of the pacemaker signal based on the start D, the peak G, and the terminal E on the original pacemaker signal. The basic morphological features of the pacemaker signal include the width, the slew rate, and the amplitude of the pacemaker signal. The width of the pacemaker signal is defined as a distance between the start D and the terminal E. The amplitude of the pacemaker signal is defined as amplitude of the peak G. The slew rate, which is a signal variation slope of the pacemaker signal, equal to a product of the amplitude and a sampling frequency divided by a product of the width and the sampling accuracy.

Step 503, confirming the pacemaker signal, that is, to determine the authenticity of the pacemaker signal. Step 503 is a process to determine whether the detected pulse signals are the true pacemaker signal or the noise interference by confirming the basic morphological features of the pacemaker signal calculated in the step 502. In detail, the basic morphological features of the pacemaker signal are compared with a number of predetermined morphologic feature ranges. The predetermined morphologic feature ranges includes a width range of the pacemaker signal, a lower limit value of the slew rate of the pacemaker signal, and a lower limit value of the amplitude of the pacemaker signal. The comparing result is used to determine whether or not the pacemaker signal is the true pacemaker signal. The pacemaker signal is considered as noise when the basic morphological features of the pacemaker signal satisfy anyone of predetermined judging conditions list below. Otherwise, the pacemaker signal is considered as the true pacemaker signal. The judging conditions include the width of the pacemaker signal is out of the predetermined width range, the slew rate of the pacemaker signal is less than the predetermined lower limit value of the slew rate of the pacemaker signal, the amplitude of the pacemaker signal is less than the predetermined lower limit value of the amplitude of the pacemaker signal, and a right amplitude of the pacemaker signal is less than a left amplitude of the pacemaker signal a predetermined difference threshold value. In the original pacemaker signal, the left amplitude is defined as an absolute value of an amplitude difference between the peak G and the start D, and the right amplitude is defined as an absolute value of an amplitude difference between the peak G and the terminal E. The predetermined difference threshold is set as the right amplitude is 0.6 times or 0.7 times of the left amplitude.

In the other embodiment, the confirmation of the pacemaker signal can employ different method according to a judgment of whether or not there is the analogous power frequency periodic noise is detected in the pre-process. For example, when the judgment of there is not the analogous power frequency periodic noise is made in the step 403, the basic morphological features of the pacemaker signal calculated in step 502 are directly confirmed in step 503. When the judgment of there is the analogous power frequency periodic noise is made in step 403, the amplitude and the slew rate calculated in step 502 is amended using the differential signal 205 at first, and the amended basic morphological features are used to confirm the pacemaker signal.

Preferably, the predetermined morphologic features ranges can be adaptive adjusted according to quality of signal. The lower limit value of the slew rate and the lower limit value of the amplitude are raised when the quality of signal fails to satisfy a quality condition. The lower limit value of the slew rate and the lower limit value of the amplitude are reduced when the quality of signal satisfy the quality condition. The quality of signal can be determined according to whether or not amplitude of the differential signal 205 in a predetermined time period satisfies the quality condition. For example, a maximum value of the differential signal 205 in a previous 2 ms period is stored in the data buffer every 2 ms. The pacemaker signal is considered as satisfying the quality condition when a frequency of the amplitude of differential signal 205 in the previous time period greater than a quality threshold value is low or the number of pacemaker signals detected in a predetermined time period is low, which means the pacemaker signal is stable. On the contrary, the pacemaker signal is considered as not satisfying the quality condition, which means the pacemaker signal is noise.

Step 504, for the current detecting channel, marking the detected pacemaker signal and recording the position of the pacemaker signal.

Step 601 further includes a detection threshold value updating step when the first boundary point A is detected in order to prepare for the next detection. An adaptive update of the detection threshold value is, in detail, to define the detection threshold value as a product of a threshold coefficient and a temporary threshold value and adaptive update the threshold coefficient and the temporary threshold value based on the differential signal 205. The threshold coefficient is adaptive updated according to the quality of the differential signal 205. The threshold coefficient defaults to 2. The threshold coefficient is increased to 3 when there is noise interference. The threshold coefficient is reduced to 1.25 when the noise is small and the differential signal 205 is stable. The temporary threshold value is adaptive updated according to a maximum value of the differential signal 205 in a time period, such as 20 ms, previous to the current time period. The adaptive update of the detection threshold value can realize precise detection of the pacemaker signal in different detection environment.

In this embodiment, the start, the terminal, and the peak of the pacemaker signal in the original pacemaker signal are determined by detecting the key points on the differential signal 205 of the original pacemaker signal. The basic morphological features of the pacemaker signal which represents characters of the pacemaker signal can be calculated from the start, the terminal, and the peak of the pacemaker signal. The authenticity of pacemaker signal can be determined based on the basic morphological features. The precision of the pacemaker signal detection is improved.

Second Embodiment

The pacemaker signal detection in the first embodiment is applied to the pacemaker signal in a single channel. In practical use, the electrocardial signal is collected by multi-channels. Some pacemaker signal may be missed due to small amplitude if only one channel is selected to detect the pacemaker signal. In order to avoid the missing of the pacemaker signal, in this embodiment, all or some channels are selected from the electrocardial signal collecting multi-channels to be employed the single channel pacemaker signal detection of the first embodiment. The position of the pacemaker signal in each channel is recorded and then the pacemaker signals detected in each single channel are combined.

Figure 10:
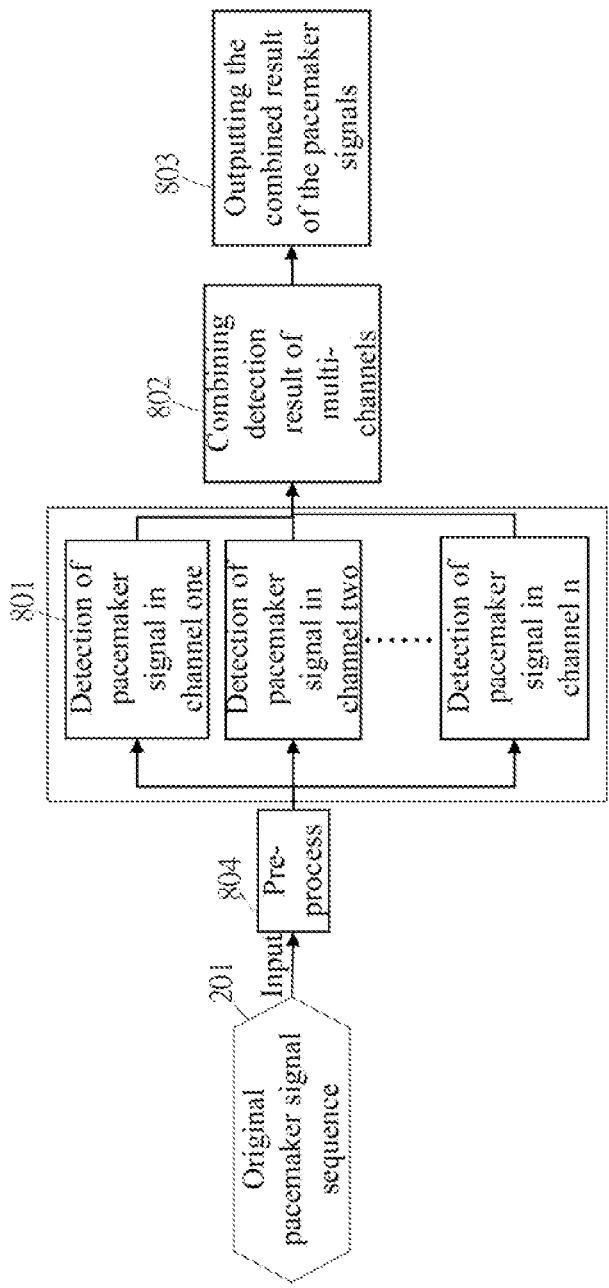
FIG. 10 is a flowchart of sub-steps for combining results of detection of the multi-channels step in a second embodiment of a pacemaker signal detecting method.

Referring to FIG. 10, in this embodiment, step 801 is executed after a pre-process to the original pacemaker signal sequence 201 in step 804. The pacemaker signal of each channel is detected based on the original pacemaker signal sequence 201. The position of the true pacemaker signal in each channel is considered as a detection result of this channel.

Step 802, combing the detection result of each channel, the combing step includes:

The true pacemaker signal in each channel of the multi-channels are detected to determine whether or not the number of the true pacemaker signal in each channel reaches a predetermined signal number threshold value.

The positions of the true pacemaker signals in the channel where the number of true pacemaker signal first reaches the predetermined signal number threshold value are considered as a combined result of the multi-channels.

A logic or operation of detection results of multi-channels is calculated when none of the number of pacemaker signals in each channel reaches the predetermined signal number threshold value. A distance between positions of two adjacent pacemaker signals in a logic or result of the true pacemaker signals of multi-channels is calculated. The two adjacent pacemaker signals are combined as one true pacemaker signal and recorded position of the combined one true pacemaker signal when the calculated distance is less than a predetermined distance threshold value. Otherwise, the two adjacent pacemaker signals are respectively considered as two true pacemaker signals and recorded the positions thereof as the logic or result of the two pacemaker signal when the calculated distance is greater than the predetermined distance threshold value.

Step 803, outputting the combined result of the true pacemaker signals. The mark of each true pacemaker signal is displayed on the electrocardial signals in each channel.

For example, the predetermined signal number threshold value is set as 2 for each channel in the predetermined time period, which can limit continuous false detections lead to high frequency noise. Position of the first detected pacemaker signal of each channel is recorded and compared with the positions of the detected pacemaker signal of the other channels when only one pacemaker signal is detected in each channel at most. Two adjacent pacemaker signals are considered as one combined pacemaker signal and the first one of the two adjacent pacemaker signals is outputted when the distance of two adjacent pacemaker signals is too small. Two adjacent pacemaker signals are respectively considered as two different pacemaker signals and outputted both of the two pacemaker signals when the distance of two adjacent pacemaker signals is greater than the predetermined distance threshold value. The pacemaker signals of each channel are directly outputted and finally combined with the pacemaker signals of the other channels when two pacemaker signals can be detected in each channel at most.

The combination of detection result of multi-channels can avoid from missing a small pacemaker signal of some channel to display the mark on the electrocardial signal. Thus, the precision of the pacemaker signal detection is improved.

Third Embodiment

Figure 11:
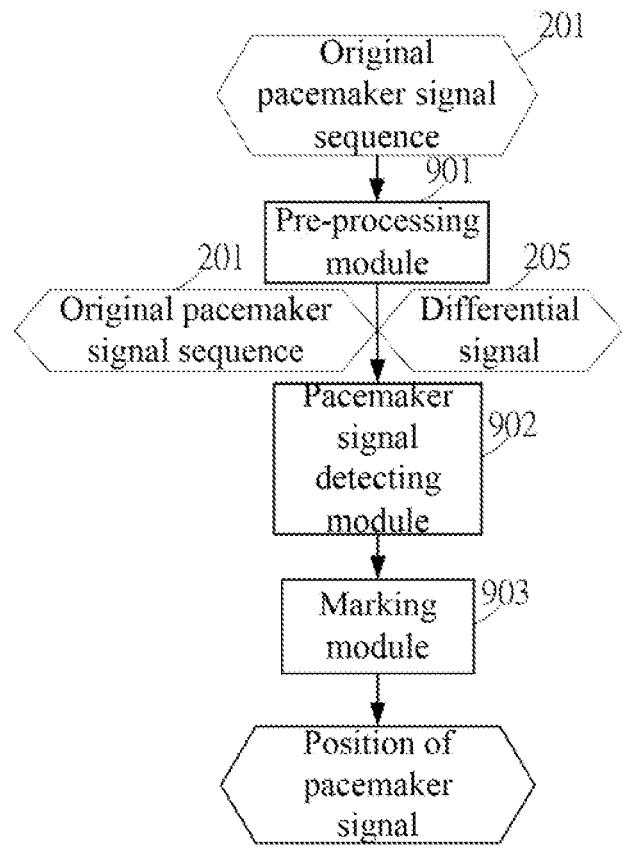
FIG. 11 is a block diagram view of an exemplary embodiment of a pacemaker signal detecting system.

Referring to FIG. 11, a pacemaker signal detecting system 13 provided in this embodiment includes a pre-processing module 901, a pacemaker signal detecting module 902, and a marking module 903.

The pre-processing module 901 pre-processes the original pacemaker signal separated from the pacemaker electrocardial signal to highlight the features of the pacemaker signal. In this embodiment, the pre-processing module 901 receives the original pacemaker signal sequence 201 from the signal acquiring system 11 and pre-processes the original pacemaker signal sequence 201.

The pacemaker signal detecting module 902 calculates the basic morphological features of the pacemaker signals based on the pre-processed original pacemaker signal and confirms the authenticity of the pacemaker signal based on the basic morphological features. The basic morphological features include the width, the slew rate, and the amplitude of the pacemaker signal.

The marking module 903 is configured to record the position of the confirmed true pacemaker signal.

Figure 12:
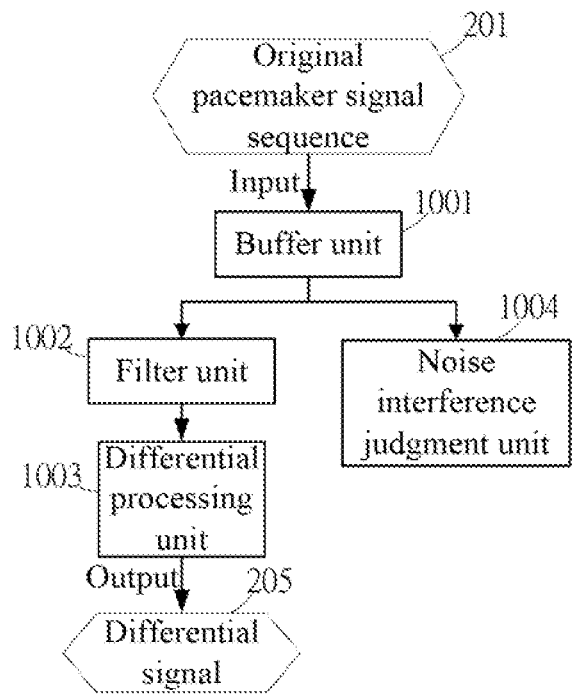
FIG. 12 is a block diagram view of a pre-processing module of the pacemaker signal detecting system.

Referring to FIG. 12, in one embodiment, the pre-processing module 901 includes a differential processing unit 1003. Preferably, the pre-processing module 901 further includes a buffer unit 1001, a filter unit 1002, and a noise interference judgment unit 1004.

The buffer unit 1001 stores the original pacemaker signal sequence 201 with the fix length to get ready to be detected. Fox example, the original pacemaker signal is set to be detected once every 2 ms. That is, the original pacemaker signal with 2 ms length is stored in the buffer unit 1001 when the original pacemaker signal is going to be detected. The detection of the original pacemaker signal is executed once every 4 ms when the fix length is set as 4 ms.

Preferably, the filter unit 1002 filters the original pacemaker signal before the differential processing unit 1003 executes a differential process to the original pacemaker signal sequence 201. The filtering process can be a band-pass filtering process or a high-pass filtering process. If the high-pass filtering process is employed, the high-pass filtering method of the above embodiment can be used.

The differential processing unit 1003 executes a differential process to the filtered original pacemaker signal to get the differential signal 205 which can highlight the features of the pacemaker signal. The differential process can employed the differential method of the above embodiment.

Preferably, the noise interference judgment unit 1004 calculates the average energy of the original pacemaker signal in the predetermined time period. In detail, the noise interference judgment module 1004 calculates the sum of the data energy stored in the buffer unit 1001. The sum of data energy means a sum of absolute value of signal of the original pacemaker signal sequence 201 stored in the buffer unit 1001. The noise interference judgment unit 1004 calculates the average energy of the original pacemaker signal in the predetermined time period according to the sum of data energy. And then, the noise interference judgment unit 1004 determines whether or not the average energy is stable according to the fluctuation of the average energy in the predetermined time period. The noise interference judgment unit 1004 compares the average energy with the predetermined energy threshold value, determines there is the analogous power frequency periodic noise of when the average energy is greater than the predetermined energy threshold value, and determines there is no the analogous power frequency periodic noise when the average energy is less than the predetermined energy threshold value.

Figure 13:
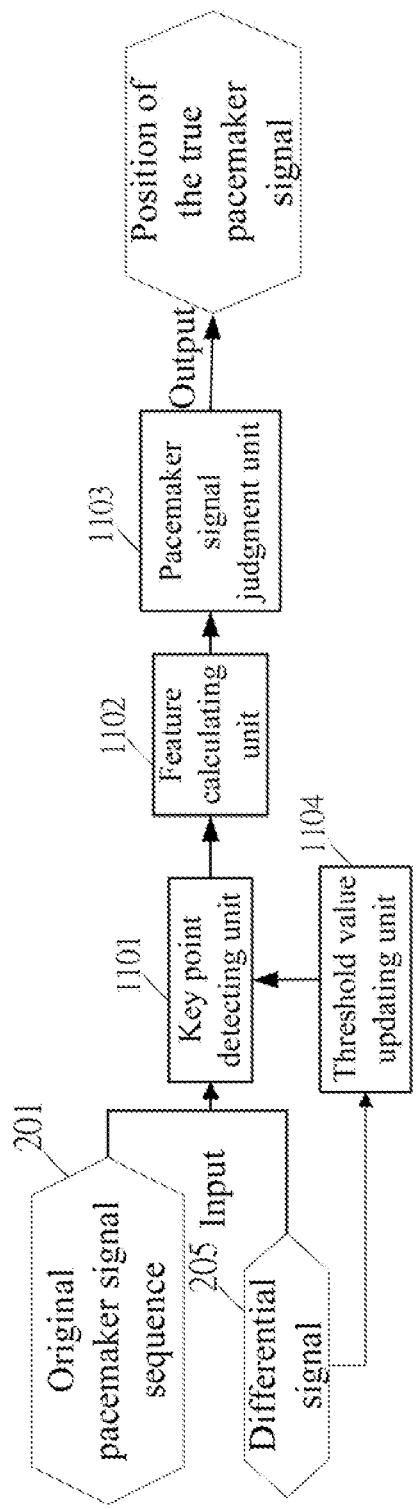
FIG. 13 is a block diagram view of a pacemaker signal detecting module of the pacemaker signal detecting system.

Referring to FIG. 13, in one embodiment, the pacemaker signal detecting module 902 includes a key point detecting unit 1101, a feature calculating unit 1102, and a pacemaker signal judgment unit 1103. Preferably, the pacemaker signal detecting module 902 further includes a threshold value updating unit 1104.

The key point detecting unit 1101 detects the start D, the terminal E, and the peak G based on the original pacemaker signal sequence 201 and the differential signal 205.

Figure 14:
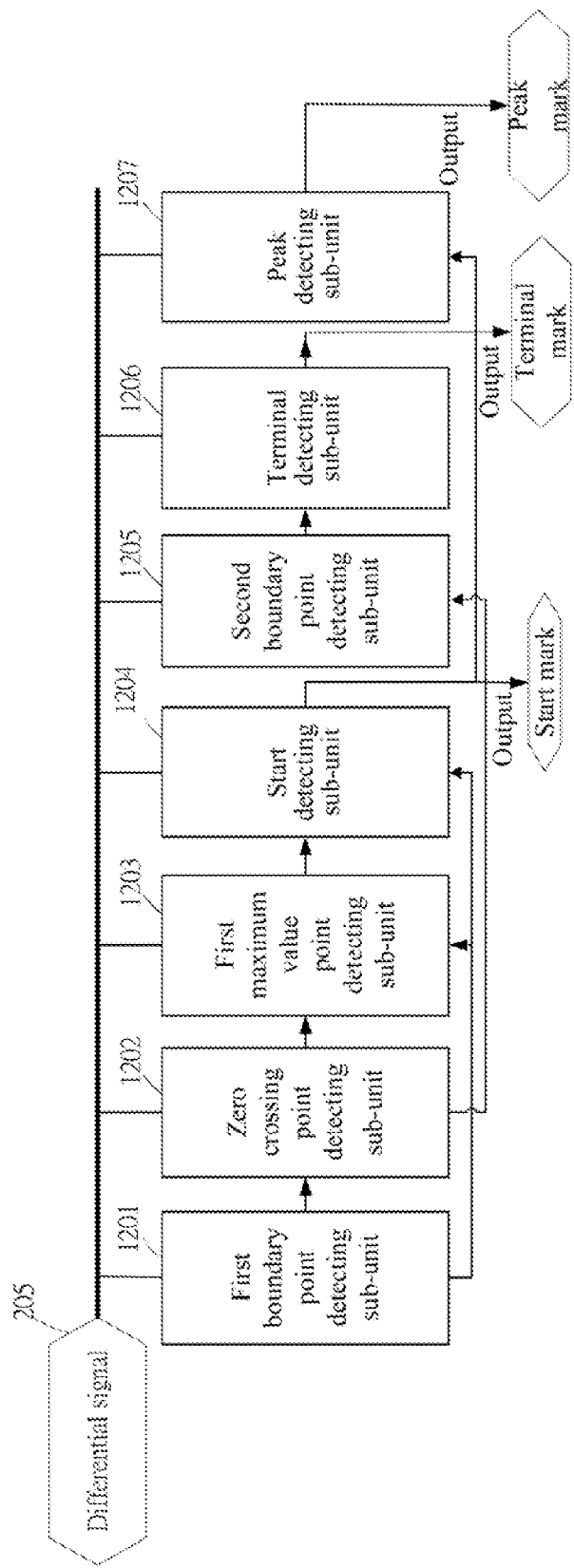
FIG. 14 is a block diagram view of a number of sub-units of a key point detecting unit in the pacemaker signal detecting module.

Referring to FIG. 14, the key point detecting unit 1101 includes a first boundary point detecting sub-unit 1201, a zero crossing point detecting sub-unit 1202, a first maximum value point detecting sub-unit 1203, a start detecting sub-unit 1204, a second boundary point detecting sub-unit 1205, a terminal detecting sub-unit 1206, and a peak detecting sub-unit 1207.

The first boundary point detecting sub-unit 1201 detects the first boundary point A on the differential signal 205 in the chronological order of detection. The first boundary point A is a point on the differential signal 205 with an absolute value first time greater than the detection threshold value. At the same time, a direction of the pacemaker signal is determined according to the first boundary point A.

The zero crossing point detecting sub-unit 1202 searches the zero crossing point B after the first boundary point A. The zero crossing point B is a first point of which the differential value sign is opposite to a differential value sign of a former point on the differential signal 205 after the first boundary point A. Preferably, a fix time period is set, to search the first point of which the differential value sign is opposite to a differential value sign of a former point on the different signal in the fix period after the first boundary point A. The zero crossing point B is defined when the first point of which the differential value sign is opposite to a differential value sign of a former point on the differential signal 205 after the first boundary point A is detected. The zero crossing point is defined as the last point on the differential signal 205 in the fix time period when the first point of which the differential value sign is opposite to a differential value sign of a former point on the differential signal 205 after the first boundary point A cannot be detected.

The first maximum value detecting sub-unit 1203 searches a maximum value with the same direction of the pacemaker signal between the first boundary point A and the zero crossing point B. The maximum value is defined as the first maximum value point.

The start detecting sub-unit 1204 detects the point satisfying conditions of the start D of the pacemaker signal before the first boundary point A and defines a point on the original pacemaker signal corresponding to the detected point as the start D of the pacemaker signal. Preferably, the conditions of the start D can be differences between a differential value of a current point and differential values of three later points are greater than differences between the differential value of the current point and differential values of three former points; or a difference between the differential value of the current point and a differential value of a later point is greater than four times of a difference between the differential value of the current point and a differential value of a former point.

The second boundary point detecting sub-unit 1205 detects the differential signal 205 after the zero crossing point B to find the second boundary point X which satisfies conditions of the second boundary point X. Preferably, the conditions of the second boundary point X can be an absolute value of the differential value of the current point is greater than half of an absolute value of the differential value of the first maximum value point C and the direction of the current point is the same as the direction of the pacemaker signal. Preferably, a fix time period is set, to detect a point satisfying the conditions of the second boundary point X in the fix time period after the zero crossing point B. The second boundary point X is defined when the point satisfying the conditions of the second boundary point X is detected. The first boundary point A is considered as interference when the point satisfying the conditions of the second boundary point X cannot be detected. Thus, this time detection of key point is terminated and then turn to the first boundary point detecting sub-unit 1201 to restart the detection of the first boundary point A with the absolute value greater than the detection threshold value.

The terminal detecting sub-unit 1206 detects a point satisfying conditions of the terminal E of the pacemaker signal after the second boundary point X and considers a point in the original pacemaker signal sequence 201 corresponding to the point satisfying conditions of the terminal E as the terminal E of the pacemaker signal. The conditions of the terminal E can be an amplitude value of a current point is close to or equal to an amplitude value of the start D. Preferably, a fix time period is set, to detect a point satisfying the conditions of the terminal E in the fix time period after the second boundary point X. The terminal E is defined when the point satisfying the conditions of the terminal E is detected. The terminal E is defined as the last point in the fix time period when the point satisfying the conditions of terminal E cannot be detected.

The peak detecting sub-unit 1207 searches the peak G between the start D and the terminal E of the original pacemaker signal sequence 201. Preferably, when the noise interference judgment unit 1004 determines there is the analogous power frequency periodic noise, a point in the original pacemaker signal corresponding to the first maximum value point C detected by the first maximum value point detecting sub-unit 1203 is considered as the peak G. When the noise interference judgment unit 1004 determines there is not the analogous power frequency periodic noise, the maximum value point having a direction the same as the direction of the pacemaker signal and between the start D and the terminal E of the original pacemaker signal is considered as the peak G of the pacemaker signal.

Referring to FIG. 13, the feature calculating unit 1102 calculates the basic morphological features of the pacemaker signal according to the start D, the terminal E, and the peak G. The basic morphological features include a width, a slew rate, and amplitude of the pacemaker signal.

The pacemaker signal judgment unit 1103 confirms the authenticity of the pacemaker signal based on the basic morphological features and determines whether the pacemaker signal is the true pacemaker signals or the reference noise. In detail, the pacemaker signal judgment unit 1103 compares the basic morphological features with the predetermined morphologic feature ranges. The predetermined morphologic feature ranges includes a width range of the pacemaker signal, a lower limit value of the slew rate of the pacemaker signal, and a lower limit value of the amplitude of the pacemaker signal. The comparing result is used to determine whether or not the pacemaker signal is the true pacemaker signal. The pacemaker signal is considered as noise when the basic morphological features of the pacemaker signal satisfy anyone of predetermined judging conditions list below. Otherwise, the pacemaker signal is considered as the true pacemaker signal. The judging conditions include the width of the pacemaker signal is out of the predetermined width range, the slew rate of the pacemaker signal is less than the predetermined lower limit value of the slew rate of the pacemaker signal, the amplitude of the pacemaker signal is less than the predetermined lower limit value of the amplitude of the pacemaker signal, and the right amplitude of the pacemaker signal is less than the left amplitude of the pacemaker signal the predetermined difference threshold value. The predetermined difference threshold is set as the right amplitude is 0.6 times or 0.7 times of the left amplitude.

Preferably, when the noise interference judgment unit 1004 determines that there is not the analogous power frequency periodic noise, the pacemaker signal judgment unit 1103 directly confirms the basic morphological features of the pacemaker signal calculated by the feature calculating unit 1102. When the noise interference judgment unit 1004 determines that there is the analogous power frequency periodic noise, the amplitude and the slew rate calculated by the feature calculating unit 1102 is amended using the differential signal 205 at first, and the amended basic morphological features are used to confirm the pacemaker signal.

In an exemplary embodiment, the pacemaker signal judgment unit 1103 adjusts the predetermined morphologic features ranges according to quality of signal. The lower limit value of the slew rate and the lower limit value of the amplitude are raised when the quality of signal fails to satisfy a quality condition. The lower limit value of the slew rate and the lower limit value of the amplitude are reduced when the quality of signal satisfy the quality condition. The quality of signal can be determined according to whether or not amplitude of the differential signal 205 in a predetermined time period satisfies the quality condition. For example, a maximum value of the differential signal 205 in a previous 2 ms period is stored in the data buffer every 2 ms. The pacemaker signal is considered as satisfying the quality condition when a frequency of the amplitude of differential signal 205 in the previous time period greater than a quality threshold value is low or the number of pacemaker signals detected in a predetermined time period is low, which means the pacemaker signal is stable. On the contrary, the pacemaker signal is considered as not satisfying the quality condition, which means the pacemaker signal is noise.

Preferably, the pacemaker signal detecting module 902 further includes a threshold updating unit 1104. The threshold updating unit 1104 adaptive updates the detection threshold value of the first boundary detection sub-unit 1201 for detecting the first boundary point A according to the differential signal 205. In detail, the detection threshold value is defined as a product of a threshold coefficient and a temporary threshold value. The threshold updating unit 1104 adaptive updates the threshold coefficient and the temporary threshold value based on the differential signal 205. The threshold coefficient is adaptive updated according to the quality of the differential signal 205. The threshold coefficient defaults to 2. The threshold coefficient is increased to 3 when there is noise interference. The threshold coefficient is reduced to 1.25 when the noise is small and the differential signal 205 is stable. The temporary threshold value is adaptive updated according to a maximum value of the differential signal 205 in a time period, such as 20 ms, previous to the current time period.

The marking module 903 marks the position of the true pacemaker signal determined by the pacemaker signal judgment unit 1103 and then output the position of the true pacemaker signal.

Figure 15:
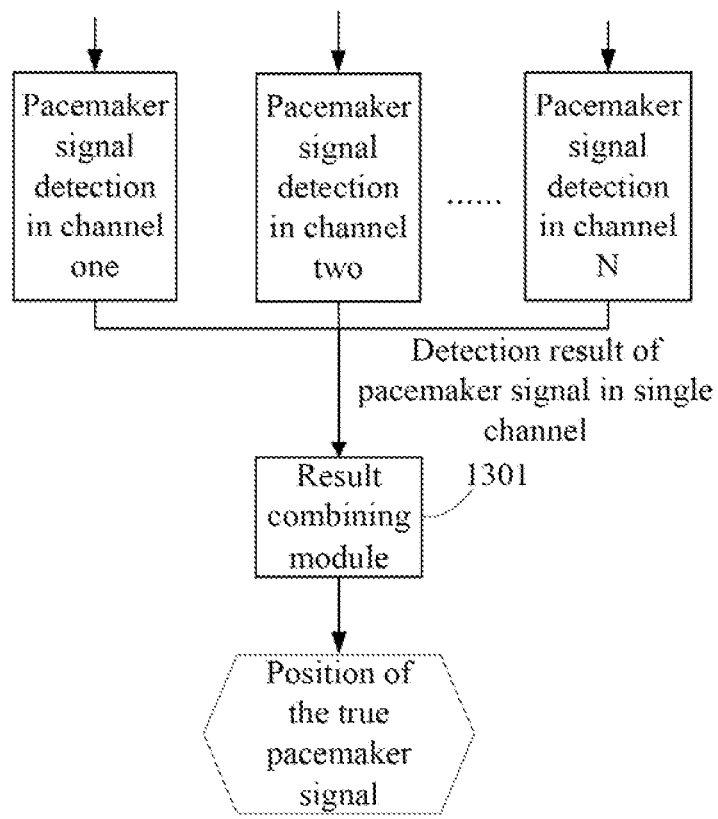
FIG. 15 is a block diagram view of a result combining module of other embodiment of the pacemaker signal detecting system.

Referring to FIG. 15, in the other embodiment, the pacemaker signal detecting system 13 further includes a result combining module 1301. The pacemaker signal of each channel is detected based on the original pacemaker signal sequence 201. The positions of the true pacemaker signal are considered as the detection result of this channel. The combined positions of the true pacemaker signal are displayed on the electrocardial signal of each channel. A specific combining way can be executed as follow:

The result combining module 1301 detects whether or not the number of the true pacemaker signal in each channel reaches the predetermined signal number threshold value. The positions of the true pacemaker signals in the channel where the number of true pacemaker signal first reaches the predetermined signal number threshold value are considered as a combined result of the multi-channels. A logic or operation of detection results of multi-channels is calculated when none of the number of pacemaker signals in each channel reaches the predetermined signal number threshold value. A distance between positions of two adjacent pacemaker signals in a logic or result of the true pacemaker signals of multi-channels is calculated. The two adjacent pacemaker signals are combined as one true pacemaker signal and recorded position of the combined one true pacemaker signal when the calculated distance is less than a predetermined distance threshold value. Otherwise, the two adjacent pacemaker signals are respectively considered as two true pacemaker signals and recorded the positions thereof as the logic or result of the two pacemaker signal when the calculated distance is greater than the predetermined distance threshold value.

The combination of detection result of multi-channels can avoid from missing a small pacemaker signal of some channel. Thus, the precision of the pacemaker signal detection is improved.

Excepting the sequential detection of the first boundary point A, the zero crossing point B, the first maximum value point C, the start D, the second boundary point X, the terminal E, and the peak G mentioned in the above embodiment, in the other embodiment, the other method can be employed to detect the start D, the terminal E, and the peak G.

For example, the first boundary point A, the zero crossing point B, the first maximum value point C, and the second boundary point X are detected in the differential signal 250. The second boundary point X can be defined as a point which is greater than the detection threshold value at the opposite direction. A second zero crossing point is searched after the second boundary point X. The peak G of the pacemaker signal is determined between the first boundary point A and the second zero crossing point. An original zero crossing point is searched in the differential signal 250 before the first boundary point A. Amplitude of the peak G is determined by a difference between the original zero crossing point and the peak G in the original pacemaker signal. The start D and the terminal E are respectively searched forwards and backwards from the peak G in the original pacemaker signal. The detection method of the start D and the terminal E is to forwards search the amplitude stable point, the reversal point, and the inflection point from the peak G as the start D of the pacemaker signal and to backwards search the amplitude stable point, the reversal point, and the inflection point from the peak G as the terminal E of the pacemaker signal.

For the other example, the first boundary point A, the zero crossing point B, the first maximum value point C, and the second boundary point X are detected in the differential signal 250. The second boundary point X can be defined as a point which is greater than the detection threshold value at the opposite direction. The peak G of the pacemaker signal is determined between the first boundary point A and the second zero crossing point. An original zero crossing point is searched in the differential signal 250 before the first boundary point A. Amplitude of the peak G is determined by a difference between the original zero crossing point and the peak G in the original pacemaker signal. The start D and the terminal E are respectively searched forwards and backwards from the peak G in the original pacemaker signal. There are two detection methods of the start D and the terminal E:

A first one, to search forwards from the peak G to find a point with an amplitude decreasing to 0.9 times of the amplitude of the peak G as the start D.

A second one, to search backwards from the peak G to find a point with an amplitude decreasing to 0.75 times of the amplitude of the peak G as the terminal E.

The above-described contents are detailed with specific and preferred embodiments for the present invention. The implementation of the present invention is not to be limited to these illustrations. For one of ordinary skill in the art, variations and equivalents having the same effects and applications can be made without departing from the spirit of the present invention and are to be considered as belonging to the scope of the present invention.

What is claimed is:

1. A pacemaker signal detecting method comprising:
acquiring a pacemaker electrocardial signal via electrodes;
separating an original pacemaker signal from the pacemaker electrocardial signal in a selected detecting channel via a signal acquiring system; and
detecting a true pacemaker signal based on the original pacemaker signal via a pacemaker signal detecting system, the step of detecting the true pacemaker signal comprising:
pre-processing the original pacemaker signal;
calculating a plurality of basic morphological features of the original pacemaker signal based on the pre-processed original pacemaker signal, wherein the basic morphological features comprise a width, a slew rate, and an amplitude of the original pacemaker signal;
confirming whether the original pacemaker signal is the true pacemaker signal based on the basic morphological features of the original pacemaker signal; and
recording positions of the original pacemaker signal confirmed as the true pacemaker signal.

2. The pacemaker signal detecting method of claim 1, wherein the pre-process of the original pacemaker signal comprises: differential processing the original pacemaker signal to obtain a differential signal; wherein the basic morphological features of the original pacemaker signal are calculated based on the differential signal and the original pacemaker signal.

3. The pacemaker signal detecting method of claim 2, wherein the basic morphological features of the original pacemaker signal are calculated according to a start point, a terminal point, and a peak point of the original pacemaker signal, the peak point of the original pacemaker signal means a point of the original pacemaker signal with a maximum amplitude value, the start point of the original pacemaker signal means an amplitude stable point, a reversal point, or an inflection point of the original pacemaker signal detected by backwards checking from the peak point in a chronological order of detection, and the terminal point of the original pacemaker signal means an amplitude stable point, a reversal point, or an inflection point of the original pacemaker signal detected by forwards checking from the peak point in the chronological order of detection.

4. The pacemaker signal detecting method of claim 3, wherein calculating a plurality of basic morphological features of the original pacemaker signal based on the pre-processed original pacemaker signal and differential signal, comprises:
detecting the start point and the terminal point of the original pacemaker signal based on the differential signal;
searching the peak point of the original pacemaker signal between the start point and the terminal point of the original pacemaker signal; and
calculating the basic morphological features of the original pacemaker signal based on the start point, the peak point, and the terminal point of the original pacemaker signal.

5. The pacemaker signal detecting method of claim 4, wherein detecting the start point and the terminal point of the original pacemaker signal based on the differential signal, comprising:

detecting a first boundary point on the differential signal in a chronological order of detection and determining a direction of the original pacemaker signal according to the first boundary point, wherein the first boundary point is a first point on the differential signal with an absolute value greater than a detection threshold value;

searching a zero crossing point after the first boundary point on the differential signal in the chronological order of detection; wherein the zero crossing point is a first point of which a differential value sign is opposite to a differential value sign of a former point on the differential signal after the first boundary point;

searching a first maximum value point with the same direction of the original pacemaker signal between the first boundary point and the zero crossing point;

searching the start point of the original pacemaker signal before the first boundary point on the differential signal in the chronological order of detection;

detecting a second boundary point after the zero crossing point on the differential signal in the chronological order of detection; and detecting the terminal point of the original pacemaker signal after the second boundary point on the differential signal in the chronological order of detection.

6. The pacemaker signal detecting method of claim 5, wherein the detection threshold value is defined as a product of a threshold coefficient and a temporary threshold value, and the threshold coefficient and the temporary threshold value are adaptive updated based on the differential signal.

7. The pacemaker signal detecting method of claim 5, further comprising:
    judging whether or not there is periodic noise, comprising:
    calculating an average energy of the original pacemaker signal in a predetermined time period and determining whether or not the average energy is stable according to a fluctuation of the average energy;
    comparing the average energy with a predetermined energy threshold value;
    determining that there is an analogous power frequency periodic noise if the average energy is greater than the energy threshold value and remains stable; and
    determining there is not the analogous power frequency periodic noise if the average energy is less than or equal to the energy threshold value or remains unstable.

8. The pacemaker signal detecting method of claim 7, wherein the first maximum value point is directly considered as the peak point of the original pacemaker signal when there is analogous power frequency periodic noise, otherwise, when there is no analogous power frequency periodic noise, detecting the start point and the terminal point of the original pacemaker signal based on the differential signal further comprises searching the peak point with the same direction of the original pacemaker signal between the start point and the terminal point of the original pacemaker signal.

9. The pacemaker signal detecting method of claim 7, wherein the calculated basic morphological features are amended using the differential signal and then the amended basic morphological features are used to confirm whether the original pacemaker signal is the true pacemaker signal when there is analogous power frequency periodic noise, and the calculated basic morphological features are directly used to confirm whether the original pacemaker signal is the true pacemaker signal when there is no analogous power frequency periodic noise.

10. The pacemaker signal detecting method of claim 1, wherein confirming whether the original pacemaker signal is the true pacemaker signal based on the basic morphological features of the original pacemaker signal, comprising:
    comparing the basic morphological features of the original pacemaker signal with a plurality of predetermined morphologic feature ranges, wherein the predetermined morphologic feature ranges comprises a width range of the true pacemaker signal, a lower limit value of the slew rate of the true pacemaker signal, and a lower limit value of the amplitude of the true pacemaker signal; and
    determining whether the original pacemaker signal is the true pacemaker signal according to a result of the comparison, wherein the original pacemaker signal is considered as a noise when any basic morphological feature of the original pacemaker signal satisfies any one of the predetermined judging conditions, otherwise the original pacemaker signal is considered as the true pacemaker signal; the predetermined judging conditions comprise:
    the width of the original pacemaker signal is out of a predetermined width range,
    the slew rate of the original pacemaker signal is less than a predetermined lower limit value of the slew rate,
    the amplitude of the original pacemaker signal is less than a predetermined lower limit value of the amplitude, and
    a difference between a right amplitude and a left amplitude of the original pacemaker signal is less than a predetermined threshold value.

11. The pacemaker signal detecting method of claim 10, wherein confirming whether the original pacemaker signal is the true pacemaker signal based on the basic morphological features of the original pacemaker signal, comprises:
    adjusting the predetermined morphologic feature ranges according to quality of the original pacemaker signal by raising the lower limit value of the slew rate and the lower limit value of the amplitude when the quality of the original pacemaker signal fails to satisfy a quality condition, and by reducing the lower limit value of the slew rate and the lower limit value of the amplitude when the quality of the original signal satisfies the quality condition.

12. The pacemaker signal detecting method of claim 1, wherein the step of detecting the true pacemaker signal based on the original pacemaker signal is employed to each channel, the positions of the true pacemaker signal are considered as a detection result of the corresponding channel; and the method further comprises:
    combining the detection result of each channel after the true pacemaker signal of each channel is detected based on the original pacemaker signal.

13. The pacemaker signal detecting method of claim 12, wherein combining the detection result of each channel comprises:
    detecting multi-channels to determine whether or not the number of the true pacemaker signals in each channel reaches a predetermined signal number threshold value;
    considering the positions of the true pacemaker signals in the channel where the number of the true pacemaker signals first reaches the predetermined signal number threshold value as a combined result of the channels; and
    calculating a logic or operation of detection results of the multi-channels when none of the number of true pacemaker signals in each channel reaches the predetermined signal number threshold value, then calculating a distance between positions of two adjacent pacemaker signals, the two adjacent pacemaker signals are combined as one true pacemaker signal and record positions of the combined true pacemaker signal when the calculated distance is less than a predetermined distance threshold value, the two adjacent pacemaker signals are respectively considered as two true pacemaker signals and record the positions thereof when the calculated distance is greater than or equal to the predetermined distance threshold value.

14. The pacemaker signal detecting method of claim 12, further comprising:

separating an electrocardial signals from the pacemaker electrocardial signal;

displaying marks of the true pacemaker signal on the electrocardial signals of each channel according to the combined detection result.

15. The pacemaker signal detecting method of claim 1, wherein pre-processing the original pacemaker signal comprises:

applying a differential process to the original pacemaker signal to obtain a differential signal;

detecting the true pacemaker signal further comprises:

detecting a plurality of key points of the original pacemaker signal based on the differential signal, the plurality of key points at least comprise a start point, a terminal point, and a peak point of the original pacemaker signal;

wherein calculating a plurality of basic morphological features of the original pacemaker signal based on the pre-processed original pacemaker signal comprises:

calculating the basic morphological features of the original pacemaker signal based on the plurality of key points.

16. The pacemaker signal detecting method of claim 15, wherein detecting a plurality of key points of the original pacemaker signal based on the differential signal comprises:

detecting a first boundary point on the differential signal in a chronological order of detection and determining a direction of the original pacemaker signal according to the first boundary point;

searching a zero crossing point after the first boundary point on the differential signal in the chronological order of detection;

searching the peak point with the same direction of the original pacemaker signal between the first boundary point and the zero crossing point;

searching the start point before the first boundary point on the differential signal in the chronological order of detection;

detecting a second boundary point after the zero crossing point on the differential signal in the chronological order of detection; and detecting the terminal point after the second boundary point on the differential signal in the chronological order of detection.

17. The pacemaker signal detecting method of claim 16, wherein the first boundary point is a first point on the differential signal with an absolute value greater than a detection threshold value;

the zero crossing point is a first point of which a differential value sign is opposite to a differential value sign of a former point on the differential signal after the first boundary point.

18. The pacemaker signal detecting method of claim 16, wherein an absolute value of a differential value of the second boundary point is greater than half of an absolute value of a differential value of the peak point and the direction of the second boundary point is the same as the direction of the original pacemaker signal.

19. The pacemaker signal detecting method of claim 16, wherein the start point and the terminal point satisfy the following conditions:

differences between a differential value of the start point or the terminal point and differential values of a predetermined number of later points are greater than differences between the differential value of the start point or the terminal point and differential values of the predetermined number of former points; or a difference between the differential value of the start point or the terminal point and a differential value of a later point is greater than a predetermined times of a difference between the differential value of the start point or the terminal point and a differential value of a former point.

* * * * *